United States Patent [19]

Comai et al.

[11] Patent Number: 5,106,739
[45] Date of Patent: Apr. 21, 1992

[54] CAMV 35S ENHANCED MANNOPINE SYNTHASE PROMOTER AND METHOD FOR USING SAME

[75] Inventors: Luca Comai, Seattle, Wash.; Paul M. Moran, San Francisco, Calif.

[73] Assignee: Calgene, Inc., Davis, Calif.

[21] Appl. No.: 477,055

[22] Filed: Feb. 7, 1990

Related U.S. Application Data

[63] Continuation-in-part of Ser. No. 339,755, Apr. 18, 1989, abandoned.

[51] Int. Cl.$^5$ .................... C12N 15/09; C12N 15/67; C12N 15/82
[52] U.S. Cl. .................. 435/172.3; 536/27; 935/30; 935/35; 435/320.1
[58] Field of Search ............. 435/172.3, 317.1, 320.1; 536/27; 935/30, 35; 339.75/5

[56] References Cited

PUBLICATIONS

Llewellyn, et al., "Structure and Expression of an Alcohol Dehydrogenase 1 Gene from *Pisum Sativum* (cv. Greenfeast)," J. Mol. Biol (1987) 195:115–123.
Ow et al. (1987) Proc. Natl. Acad. Sci., USA 84: 4870–4874.
DiRita et al. (1987) Mol. Gen. Genetics 207: 233–241.
Chen et al. (1988) The EMBO Journal 7(2): 297–302.
Kay et al. (1987) Science 236: 1299–1302.
Fang et al. (Jan. 1989) The Plant Cell 1: 141–150.
Odell et al. (1988) Plant Molecular Biology 10: 263–272.
Ellis et al. (1987) The EMBO Journal 6(1): 11–16.

*Primary Examiner*—Elizabath C. Weimar
*Assistant Examiner*—Che Swyden Chereskin

[57] ABSTRACT

Unexpectedly high levels of expression of coding sequences can be obtained by the use of a CaMv 35s enhanced mannopine synthase promoter in plant host cells.

21 Claims, 8 Drawing Sheets

Page 1 of 2

Page 2 of 2

CAMV 35S ENHANCED MANNOPINE SYNTHASE PROMOTER AND METHOD FOR USING SAME

CROSS REFERENCE TO RELATED APPLICATION

This is a continuation-in-part of U.S. application Ser. No. 07/339,755, filed Apr. 18, 1989, now abandoned which disclosure is incorporated by reference.

FIELD OF THE INVENTION

This invention relates to improvements in a plant promoter to increase the level of transcription of a coding sequence regulated thereby.

BACKGROUND

Eukaryotic genes consist of a transcription/translation initiation region, a coding region and a termination region. The transcription/translation initiation region is typically located upstream of the coding region, or in other words, entirely to the 5' terminal end of the coding region. This initiation region includes a "promoter" region, the element responsible for inducing transcription and "untranslated sequences" responsible for binding to ribosomes and translation initiation. The translation-related regions of these "upstream" regulatory sequences are sometimes referred to as the "mRNA untranslated leader." They vary in length and base composition from gene to gene.

The characteristics of the promoter will determine the level and timing of transcription. A promoter typically consists of a "TATA box" and an "upstream activating region" (sometimes referred to herein as "UAR"). The TATA box is responsible for marking the initiation of transcription approximately $-25$ or 25 base pairs in the 3' direction toward the start of the coding region. Through recombinant techniques, a plant transcription/translation initiation region can be designed to activate a nucleic acid sequence of interest, such as a DNA sequence encoding a heterologous or non-naturally occurring gene, in a plant host cell. And by modifying the promoter region of a construct capable of expression in a plant host cell, timing and the level of expression of transcription can be controlled.

As noted above, recombinant DNA technology is now being applied to plants. Researchers are able to modify plant genetic material and achieve expression of proteins of interest in a plant host cell, for example. However, it is often desired to increase the expression of the nucleic acid sequence of interest. Higher levels of expression may be desired to increase the level of the desired protein in the consumer product, to have a desired enzymatic or other effect on a plant cell biochemical pathway, to create more anti-sense copies of an endogenous gene thereby reducing the amount of mRNA transcript which could then be processed by the cell, or the like. Methods to achieve increased plant cell expression include the search for stronger promoters, gene amplification, and use of enhancer regions to boost the expression level of weaker promoters.

RELEVANT LITERATURE

Khoury & Gruss, *Cell* (1983) 33:313-314, is a background article on enhancer elements generally.

Kay, et al, *Science* (1987) 236:1299-1302 reports the use of a duplicated homologous promoter system (a "double" CaMV 35S promoter) as an enhancer. Another group of researchers, Odell, et al, *Plant Mol. Bio.* (1988) 10:263-272, have reported the use of a CaMv 35S promoter fragment as an enhancer to the nopaline synthase promoter (NOS) and reported an increase in the level of expression of a chloramphenicol acetyltransferase (CAT) under the control of the weak NOS promoter to the level observed in the intact CaMV 35S promoter. Ellis, et al, *EMBO* (1987) 6:11-16, reports the use of an octopine synthase (ocs) promoter fragment and also alternatively, a CaMV 35S promoter fragment, to enhance the promoter activity of the maize alcohol dehydrogenase gene (Adh-1) in tobacco over the weak activity of the Adh-1 promoter alone.

The complete nucleotide sequence of the octopine Ti T-DNA, including sequences corresponding to the mannopine synthase gene (Open Reading Frame 24), is reported in Barker, et al, *Plant Mol. Bio.* (1983) 2:335-350.

Other references of interest include: Odell, et al, *Nature* (1985) 313:810-812;; DiRita & Gelvin, *Mol Gen Genet* (1987) 207:233-241; Gelvin, et al, *Mol Gen Genet* (1985) 199:240-248; Velten, et al, *EMBO* (1984) 3:2723-2730; Comai, et al, *Nature* (1985) 317:741.

SUMMARY OF THE INVENTION

Unexpectedly high levels of expression of coding sequences can be obtained by the use of a CaMV 35S-enhanced mannopine synthase promoter in plant host cells.

A DNA sequence of this invention will comprise in the 5' to 3' direction, a first element linked to a second element, said first element comprising an upstream activating region of CaMV 35S and said second element comprising a mannopine synthase transcription initiation region or promoter. More specifically, the first element may correspond to approximately about a 200 bp to about 800 bp fragment, preferably from about nucleotide $-360$ to about $-90$ of the CaMV 35S gene, and the second element may correspond to approximately about 325 bp to about 800 bp of the transcription or transcription/translation region of the mannopine synthase gene. In one embodiment, the second element may include from about nucleotide $-625$ to about $+60$ of the transcription/ translation region of the mannopine synthase gene. A shorter mannopine synthase transcription/translation element may also be used, such as from about nucleotide $-300$ to about $+60$ of the upstream region of the mannopine synthase gene.

In a different embodiment, the invention is directed to a chimeric promoter comprising a CaMV 35S-enhanced mannopine synthase promoter, wherein upon expression of a DNA sequence of interest in a plant cell under the regulatory control of the enhanced promoter, said DNA sequence of interest is expressible at a level of at least 5-fold higher than expression of the gene of interest in a plant cell under the regulatory control of a CaMV 35S-enhanced CaMV 35S promoter.

In yet a different embodiment, this invention relates to a process of increasing the expression of an expressible gene of interest under the regulatory control of a mannopine synthase promoter by linking a CaMV 35S upstream activating region to the 5' end of a mannopine synthase promoter and allowing the gene to be expressed.

DETAILED DESCRIPTION OF THE INVENTION AND PREFERRED EMBODIMENTS

By this invention, the activity of a mas transcription initiation region, and in particular, the promoter function of the mas transcription/translation initiation region are synergistically enhanced by providing a CaMV 35S upstream activating region ("UAR") to the 5' end of a mannopine synthase ("mas") transcription/translation initiation region. Because the UAR of the CaMV 35S enhances the functions of the mas transcription or transcription/translation initiation region, the resulting DNA sequences are considered to result in an "enhanced mas promoter." The enhanced mas promoter of this invention may also be referred to as a "MAC" promoter herein, for convenience.

The term "transcription/translation initiation region of mannopine synthase" as used herein refers to sequences comparable to the DNA sequences responsible for initiating transcription and effecting translation of the mannopine synthase gene derived from the TR-DNA of the octopine Ti plasmid. A DNA sequence comprising the complete transcription/translation initiation region of the mannopine synthase (also sometimes referred herein as "mas") gene corresponds to those DNA sequences found approximately from about $-625$ basepairs upstream of the transcriptional start site of the mannopine synthase structural gene to about $+60$ basepairs downstream of the start site of the mannopine synthase gene, approximately about 685 base pairs. Fragments of the mas transcription/translation initiation region may also be used as long as the sequence is capable of effecting efficient transcription and translation of a coding sequence under its regulatory control. For example, a sequence from about $-300$ to about $+60$ of this region is acceptable. Alternatively a sequence from about $-300$ to about the start codon is acceptable.

The term "mannopine synthase promoter" as used herein refers to DNA sequences, or elements, comparable to the sequences responsible for inducing transcription of mannopine synthase. Thus, by definition, the mas promoter region is included within the transcription/translation initiation regions of the mas gene.

The term "upstream activating region of CaMV 35S" herein refers to DNA sequences comparable to the CaMV 35S promoter region, absent the TATA box, i.e., the upstream activating region ("UAR") of CaMV 35S.

Preferably, the 3' end of the UAR is no greater than from about nucleotide $-25$. More preferred is a 3' end of no greater than from about nucleotide $-45$, and most preferred is a 3' end of no greater than about nucleotide $-90$. Extending in the 5' direction, a terminus at about nucleotide $-168$ is preferred. A more preferred embodiment includes up to about nucleotide $-360$ at the 5' terminus.

Figure 1:
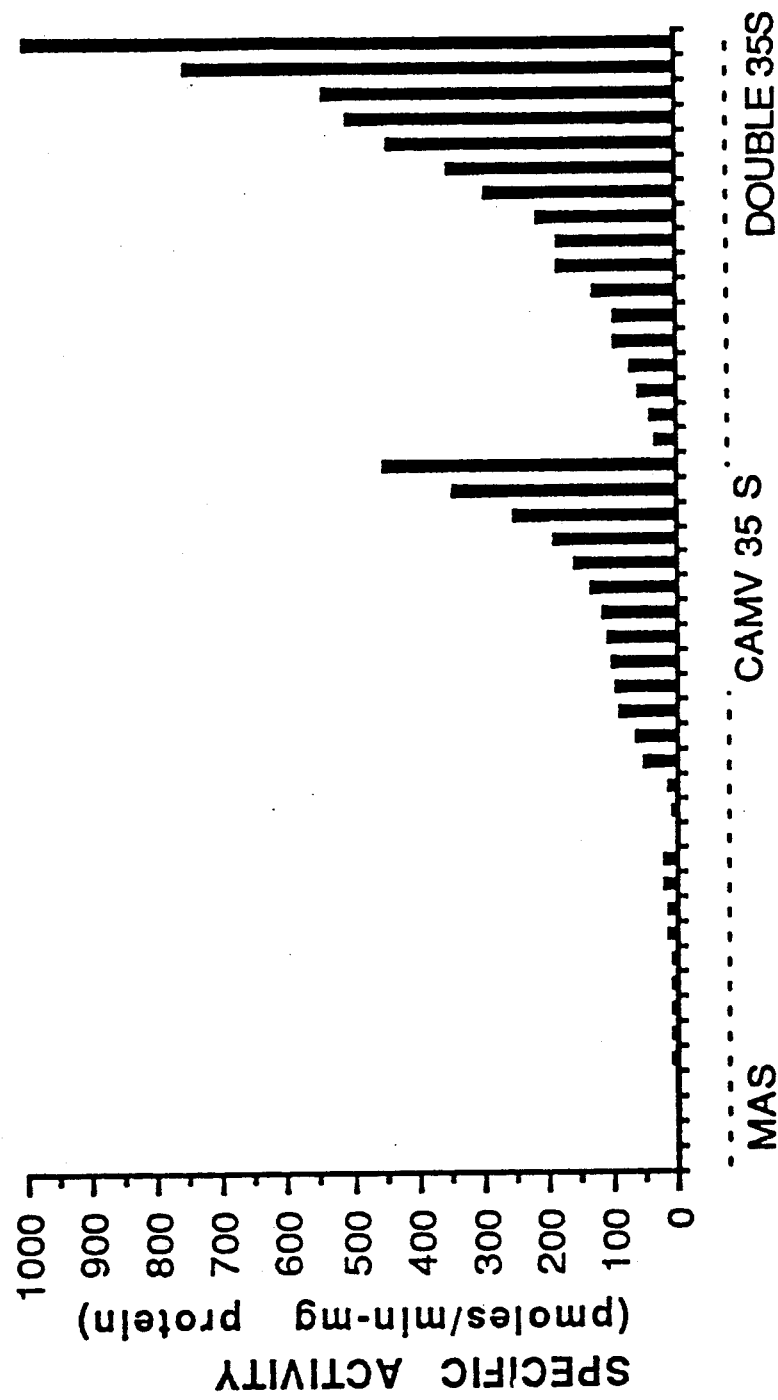
FIG. 1 is a graph showing a comparison of gus activity of several transformants under the control of a transcription/translation initiation region having a mas promoter, a CaMV 35S promoter, or a double CaMV 35S promoter.

Without the enhancing element of the CaMV 35S UAR as provided by this invention, the mas promoter is a weak promoter. The mas promoter is reported to initiate transcription of heterologous genes in plants at levels below those obtained with a CaMV 35S promoter. Data comparing the activity of the mas promoter to a gus/mas3' construct having a CaMV 35S promoter or a double 35S promoter is shown in FIG. 1. The mas promoter has been found to show expression in all plant tissues but at different levels. It is most highly expressed in apical shoots and roots and precambium tissue. In addition, there is evidence which suggests that the mas promoter is wound-inducible, causing increased expression in leaves wounded by insect chewing, for example.

Surprisingly, it has been discovered that the MAC promoter can induce the expression of a gene to levels of about 5-fold, and up to approximately ten-fold, higher than the relating strong double CaMV 35S promoter. This finding was unexpected and novel. It indicates that the elements from the CaMV 35S and mas promoters have a synergistic effect which could not be predicted. The MAC promoter will thus be useful in a number of applications where high levels of expression are desired. It may find particular application in rapidly dividing tissues or wounded-tissues.

The upstream activating region of CaMV 35S and the mannopine synthase promoter may be linked together according to conventional means to provide the MAC promoter herein. It is preferred that the UAR CaMV 35S element and the mannopine synthase promoter element are located in close proximity to one another. Most preferred is a ligation joining the two elements as directly as possible i.e., with as few intervening DNA sequences as possible. It is preferred that the mannopine synthase promoter element is provided within the translation/transcription initiation region of mannopine synthase, i.e., it is preferred that the CaMV35S UAR is linked to the transcription/translation initiation region of mannopine synthase. When the mannopine synthase promoter is provided with the translation/transcription initiation region of mannopine synthase the mannopine synthase mRNA untranslated region will be provided.

An expression cassette of this invention, will comprise, in the 5' to 3' direction, the MAC promoter, in reading frame, one or more nucleic acid sequences of interest followed by a transcript termination region. The expression cassette may be used in a variety of ways, including for example, insertion into a plant cell for the expression of the nucleic acid sequence of interest. The particular methods used to transform such plant cells are not critical to this invention, nor are subsequent steps, such as regeneration of such plant cells, as necessary. Any method or combination of methods resulting in the expression of the desired sequence or sequences under the control of the MAC promoter is acceptable.

At the 3' terminus of the structural gene will be provided a termination region which is functional in plants. A wide variety of termination regions are available that may be obtained from genes capable of expression in plant hosts, e.g., bacterial, opine, viral, and plant genes. Suitable transcript termination regions include termination regions known to those skilled in the art, such as the nos 3', tml 3', or acp 3', for example. It is preferred that a mannopine synthase gene transcript termination region (mas 3') be used in conjunction with the MAC promoter.

In preparing the constructs of this invention, the various DNA fragments may be manipulated, so as to provide for the DNA sequences in the proper orientation and, as appropriate, in the proper reading frame. Toward this end, adapters or linkers may be employed for joining the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, or the like may be employed, where insertions, deletions or substitutions, e.g., transitions and transversions, may be involved.

By appropriate manipulations, such as restriction, chewing back or filling in overhangs to provide blunt ends, ligation of linkers, or the like, complementary ends of the fragments can be provided for joining and ligation.

It is contemplated that sequences corresponding to the above noted sequences may contain one or more modifications in the sequences from the wild-type but will still render the respective elements comparable with respect to the teachings of this invention. For example, as noted above, fragments may be used, different codons or groups of codons may be modified, added or deleted in keeping with the instant invention. The sequences themselves may be a composite of segments derived from a plurality of sources, naturally occurring or synthetic.

In carrying out the various steps, cloning is employed, so as to amplify the amount of DNA and to allow for analyzing the DNA to ensure that the operations have occurred in a proper manner. A wide variety of cloning vectors are available, where the cloning vector includes a replication system functional in *E. coli* and a marker which allows for selection of the transformed cells. Illustrative vectors include pBR322, pUC series, M13 mp series, pACYC184, etc. Thus, the sequence may be inserted into the vector at an appropriate restriction site(s), the resulting plasmid used to transform the *E. coli* host, the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

In addition to the transcription construct, depending upon the manner of introduction of the transcription construct into the plant, other DNA sequences may be required. For example, when using the Ti- or Ri-plasmid for transformation of plant cells, as described below, at least the right border and frequently both the right and left borders of the T-DNA of the Ti- and Ri-plasmids will be joined as flanking regions to the transcription construct. The use of T-DNA for transformation of plant cells has received extensive study and is amply described in EPA Serial No. 120,516, Hoekema, In: The Binary Plant Vector System Offset-drukkerij Kanters B.V., Alblasserdam, 1985, Chapter V, Fraley, et al., *Crit. Rev. Plant Sci.*, 4:1–46, and An et a al., *EMBO J.* (1985) 4:277–284.

Alternatively, to enhance integration into the plant genome, terminal repeats of transposons may be used as borders in conjunction with a transposase. In this situation, expression of the transposase should be inducible, or the transposase inactivated, so that once the transcription construct is integrated into the genome, it should be relatively stably integrated and avoid hopping.

The transcription construct will normally be joined to a marker for selection in plant cells. Conveniently, the marker may be resistance to a biocide, particularly an antibiotic, such as kanamycin, G418, bleomycin, hygromycin, chloramphenicol, or the like. The particular marker employed will be one which will allow for selection of transformed cells as compared to cells lacking the DNA which as been introduced.

Examples of some methods known in the art for transformation of plant cells include transformation via *Agrobacterium tumefaciens*, electroporation, microinjection, and bombardment with DNA coated particles. Examples of DNA sequences of which high level expression may be desired include mutated aroA genes which provide glyphosate herbicide resistance, nitrilase genes which provide bromoxynil resistance, heat shock proteins, anti-sense DNA sequences to reduce the level of an endogenous protein and the like.

Various plants or plant cell cultures may be used. Plant cell cultures may be desirable as model test systems or for the efficient production of various products. Examples of plants and plant cells which may be used include tobacco, tomato, cotton, rapeseed, soybean, maize, wheat, rice, alfalfa, potato, as representative examples.

By this invention, it is also anticipated that a "double" CaMV 35S UAR may be used to enhance the mas promoter. Thus, in the 5' to 3' direction would be found a first CaMV 35S UAR element linked to a second CaMV 35S UAR element, linked to a DNA sequence comprising the mas promoter. A mas promoter enhanced by a "double CaMV 35S UAR" may be used in the same manner as described with respect to the MAC promoter. Tests indicate that the double CaMV 35S UAR enhanced mas ("Double MAC") promoter also provides up to about ten-fold increases in expression over a double CaMV 35S promoter.

The following examples are offered by way of illustration and not by way of limitation.

EXPERIMENTAL

Construction of Plasmids

1. UAR CaMV 35S/Mas Promoter

Figure 2:
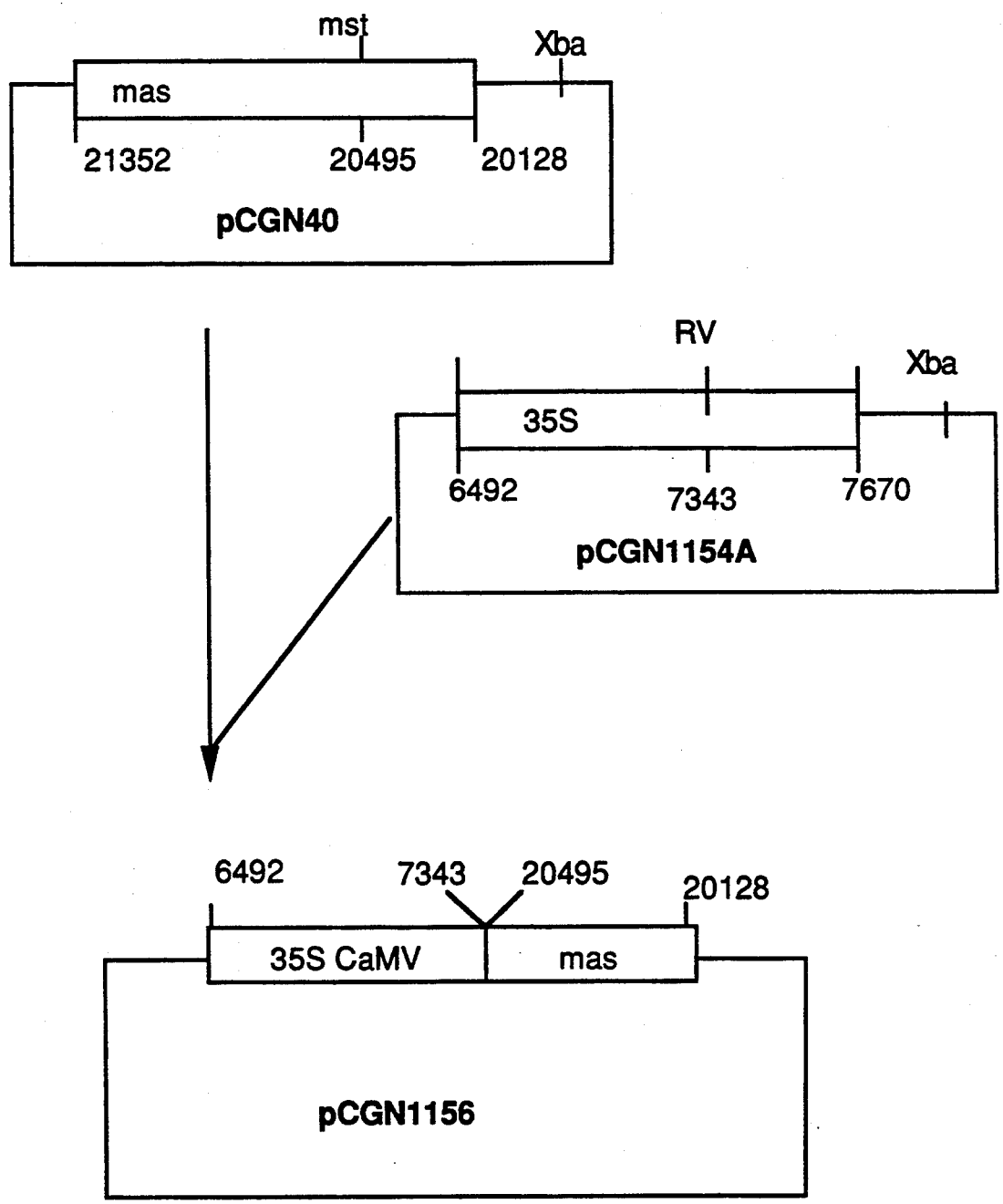
FIG. 2 represents the final construction steps of and a plasmid map of pCGN1156.

A BglII digested 1178 bp fragment containing the 5' promoter region of the CaMV 35S genome (nucleotides 6492 to 7670 as published by Gardner, et al., *Nucleic Acids Res.* (1981) 9:2871–2888) is cloned into the BamH1 site of pUC19 (Norrander, et al, Gene (1983) 26:101–106), resulting in pCGN1154A. pCGN1154A is digested with EcoRV and XbaI, deleting the TATA box containing region of the CaMV 35S, and in its place, a fragment containing the TATA box and about 300 bp of the 5' upstream region of the mas transcription/translation regulatory region (specifically, nucleotides 20495 to 20128 as published by Barker, et al., *Plant Molecular Bio.* (1983) 2:335–350) is inserted. FIG. 2. The resulting plasmid, pCGN1156, contains the hybrid UAR of CaMV 35S/mas promoter (the "MAC"). This plasmid is digested with SmaI for insertion of an XhoI linker, resulting in pCGN1156-XhoI.

pCGN7000 is digested with XbaI and PstI and the resulting fragment containing the gus gene and the mas 3' is inserted into XbaI, PstI digested pCGN1156-XhoI.

Expression Construct pCGN7000 is prepared from BamHI, SacI digested pCGN1052 and pBI221.1 (Jefferson, R. A., *Plant Mol. Bio.Rep* (1987) 5:387–405). The BamHI, SacI fragment containing the beta glucuronidase gene is excised from pBI221.1 and inserted into pCGN1052, resulting in pCGN7000. pCGN1052 is an expression plasmid containing the 5' and the 3' region of the mas gene, separated by a polylinker,. 5' TCTAGAGGATCCCGG-GTACCGAGCTCGAATTC 3'. pCGN7000 is then digested with XbaI and PstI, and fragment containing the gus gene and the mas 3' inserted into XbaI and PstI digested pCGN1156-Xho resulting in p"code 7-004". This plasmid contains a MAC 5'-gus-mas 3' chimeric gene flanked by Xho1 sites.

The next steps are designed to add PstI and BglII sites to an XhoI fragment. PCGN566, which contains the EcoRI-HindIII linker of pUC18 (Yanish-Perron, et al., Gene (1985) 53:103–119) inserted into the EcoRI-HindIII sites of pUC13-cm (K. Buckley, Ph.D. Thesis, UC San Deigo 1985) is digested with HindIII and EcoR1 and thereafter inserting a synthetic oligonucleotide having the region 5' AAGCTTAGATCTCT-GCAGCTCGAGCTGCAGAGATCTGAATTC 3' making a polylinker (having the following sites: HindIII, BglII, PstI, XhoI, PstI, BglII and EcoRI) to create pCGN7329.

Figure 3:
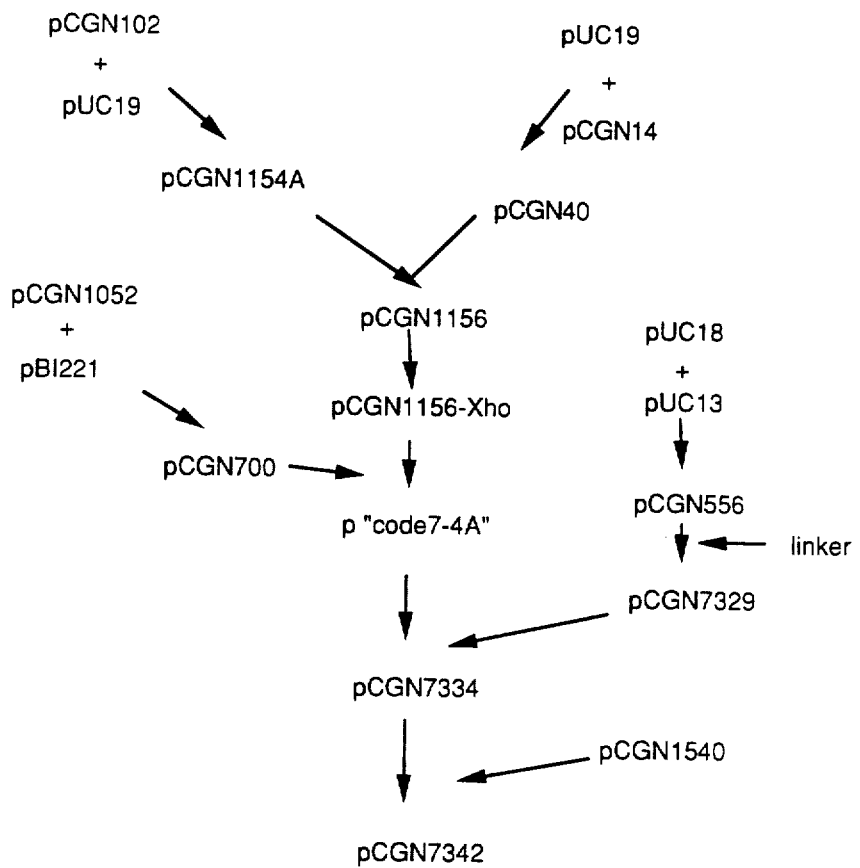
FIG. 3 is a schematic representation of the steps used to create pCGN7342.

The MAC-gus-mas gene of XhoI digested p7-004 is inserted into XhoI digested pCGN7329 creating pCGN7334. This construct is digested with PstI and the MAC-gus-mas gene inserted into the PstI site of the binary vector pCGN1540 (described below) resulting in pCGN7342. FIG. 3.

Binary Vector pCGN1540 pCGN1540 is a binary plant transformation vector containing the left and right T-DNA borders of *Agrobacterium tumefaciens* octopine Ti-plasmid pTiA6 (Currier and Nester, *J. Bact.* (1976) 126:157–165), the gentamycin resistance gene of pHiJI (Hirsch and Beringer, *Plasmid* (1984) 12:139–141), an *Agrobacterium rhizogenes* Ri plasmid origin of replication from pLJB11 (Jouanin et al., *Mol. Gen. Genet.* (1985) 201:370–374), the mas promoter region and mas 3' region of pTiA6 with the kanamycin resistance gene of Tn5 (Jorgensen et al., *Mol. Gen. Genet.* (1979) 177:65), a ColE1 origin of replication from pBR322 (Bolivar et al., *Gene* (1977) 2:95–133), and a lacZ' screenable marker gene from pUC18 (Norrander et al., *Gene* (1983) 26:101–106). The backbone of pCGN1540, containing the gentamycin resistance gene and the Ri and ColE1 origins, is derived from pCGN1532 (see below). The Ti borders and plant selectable marker gene (mas5'-kan-mas3'), are from pCGN1537; the plant selectable marker cassette is in turn taken from pCGN1536 (see below), while the right border and the lacZ' fragments are derived from pCGN565RBα2X, and the left border derived from pCGN65.

A. pCGN1532 construction.

The 3.5 kb EcoRI-PstI fragment containing the gentamycin resistance gene is removed from pPh1JI (Hirsch and Beringer, *Plasmid* (1984) 12:139–141) by EcoRI-PstI digestion and cloned into EcoRI-PstI digested pUC9 (Vieira and Messing, *Gene* (1982) 19:259–268) to generate pCGN549. HindIII-PstI digestion of pCGN549 yields a 3.1 kb fragment bearing the gentamycin resistance gene, which is made blunt ended by the Klenow fragment of DNA polymerase I and cloned into PvuII digested pBR322 (Bolivar et al., *Gene* (1977) 2:95–113) to create pBR322Gm. pBR322Gm is digested with DraI and SphI, treated with Klenow enzyme to create blunt ends, and the 2.8 kb fragment cloned into the Ri origin-containing plasmid pLJbB11 (Jouanin et al., *Mol. Gen. Genet.* (1985) 201:370–374) which has been digested with ApaI and made blunt-ended with Klenow enzyme, creating pLHbB11Gm. The extra ColE1 origin and the kanamycin resistance gene are deleted from pLHbB11Gm by digestion with BamHI followed by self closure to create pGmB11. The HindII site of pGmB11 is deleted by HindIII digestion followed by treatment with Klenow enzyme and self closure, creating PGmB11H. The PstI site of pGmB11-H is deleted by PstI digestion followed by treatment with Klenow enzyme and self closure, creating pCGN1532.

B. pCGN1536 construction.

The 5.4 kb EcoRI fragment is removed from pVK232 (Knauf and Nester, *Plasmid* (1982) 8:45), by EcoRI digestion and cloned into EcoRI digested pACYC184 (Chang and Cohen, *J. Bacteriol.* (1978) 134:1141–1156) to create pCGN14. The 1434 bp ClaI-SphI fragment of pCGN14, containing the mas 5' region (bp20128-21562 according to numbering of (Barker et al., *Plant Mo. Biol.* (1983) 2:335–350) is cloned into AccI-SphI digested pUC19 (Yanisch-Perron et al., *Gene* (1985) 33:103–119) to generate pCGN40. A 746 bp EcoRV-NaeI fragment of the mas 5' region is replaced by an XhoI site by digesting pCGN40 with EcoRV and NaeI followed by ligation in the presence of a synthetic XhoI linker DNA to create PCGN1036. The 765 bp SstI-HindIII fragment (bp 18474-19239) of pCGN14, containing the mas 3' region, is cloned into SstI-HindIII digested pUC18 (Norrander et al., *Gene* (1983) 26:101–106) to yield pCGN43. The HindIII site of pCGN43 is replaced with an EcoRI site by digestion with HindIII, blunt ending with Klenow enzyme, and ligation of synthetic EcoRI linker DNA to create pCGN1034. The 767 bp EcoRI fragment of pCGN1034 is cloned into EcoRI-digested pCGN1036 in the orientation that places bp 19239 of the mas 3' region proximal to the mas 5' region to create pCGN1040. CGN1040 is subjected to partial digestion with SstI, treated with T4 DNA polymerase to create blunt ends, and ligated in the presence of synthetic XhoI linker DNA; a clone is selected in which only the SstI site at the junction of bp 18474 and vector DNA (constructed in pCGN43 and carried into pCGN1040) is replaced by an XhoI site to generate pCGN1047.

pCGN565 (a cloning vector based upon pUC8-cm but containing pUC18 linkers) is digested with EcoRI and HindIII, treated with Klenow enzyme to create blunt ends, and ligated in the presence of synthetic XhoI linker DNA to create pCGN1003; this recreates the EcoRI site adjacent to the XhoI linker. pCGN1003 is digested with EcoRI, treated with Klenow enzyme to create blunt ends, and ligated in the presence of synthetic PstI linker DNA to create pCNG1007. The 1.5 kb XhoI fragment of pCGN1047, containing the mas 5' region and the mas 3' region with multiple cloning sites between, is cloned into XhoI digested pCGN1007 to construct pCGN1052. A portion of the multiple cloning site of pCGN1052 is deleted by digestion with SbaI and SstI, treated with Klenow enzyme to make blunt ends, and ligated to generate pCGN1052ΔXS.

The 1 kb EcoRI-SmaI fragment of pCNG783 (pCGN783 is a binary plasmid containing the left and right T-DNA borders of *A. tumefaciens* (Barker et al., *Plant Mol. Biol.* (1983) 2:335–350); the gentamicin resistance gene of pPH1JI (Hirsch et al., *Plasmid* (1984), 9:2871-2890), the kanamycin resistance gene of Tn5 (Jorgenson et al, infra and Wolff et al., ibid (1985) 13:355-367) and the 3' region from transcript 7 of pTiA6 (Barker et al., supra (1983). The plasmid pCGN783 has been deposited with ATCC (Rockville, Md.), accession number 67868, dated Dec. 23, 1988.), containing the 1 ATG-kanamycin resistance gene, is cloned into EcoRI-SmaI digested Bluescript M13KS (Strategene, Inc., Calif.) to create pBSKm; this plasmid contains an M13 region allowing generation of single stranded DNA. Single stranded DNA is generated according to the supplier's recommendations, and in vitro mutagenesis is performed (Adelman et al., *DNA* (1983) 2:183–193) using a synthetic oligonucleotide with the sequence 5'GAACTCCAGGACGAGGC3' to alter a PstI site with the kanamycin resistance gene and make it undigestable, creating pCGN1534. pCGN1534 is digested with SmaI and ligated in the presence of synthetic EcoRI linker DNA to generate pCGN1535.

The 1 kb EcoRI fragment of pCGN1535 is cloned into EcoRI digested pCGN1052ΔXS to create the mas5'-kan mas3' plant selectable marker cassette pCGN1536.

C. pCGN565RBα2X construction.

pCGN45I (see below) is digested with HpaI and ligated in the presence of synthetic SphI linker DNA to generate pCGN55. The XhoI-SphI fragment of PCGN55 (bp13800-15208, including the right border, of *Agrobacterium tumefaciens* T-DNA; (Barker et al., *Gene* (1977) 2:95–113) is cloned into SalI-SphI digested pUC19 (Yanisch-Perron et al., *Gene* (1985) 53:103–119) to create pCGN60. The 1.4 kb HindIII-BamHI fragment of pCGN60 is cloned into HindIII-BamHI digested pSP64 (Promega, Inc.) to generate PCGN1039. pCGN1039 is digested with SmaI and NruI (deleting bp14273-15208; (Barker et al., *Gene* (1977) 2:95–113) and ligated in the presence of synthetic BglII linker DNA creating pCGN1039ΔNS. The 0.47 kb EcoRI-HindIII fragment of pCGN1039ΔNS is cloned into EcoRI-HindIII digested pCGN565 to create pCGN565RB. The HindIII site of pCGN565RB is replaced with an XhoI site by digesting with HindIII, treating with Klenow enzyme, and ligating in the presence of synthetic XhoI linker DNA to create pCGN565RB-H+X.

pUC18 (Norrander et al., *Gene* (1983) 26:101–106) is digested with HaeII to release the lacZ' fragment, treated with Klenow enzyme to create blunt ends, and the lacZ'-containing fragment ligated into pCGN565RB-H+X, which had been digested with AccI and SphI and treated with Klenow enzyme in such a orientation that the lacZ' promoter is proximal to the right border fragment; this construct, pCGN565RBα2x is positive for lacZ' expression when plated on an appropriate host and contains bp 13990-14273 of the right border fragment (Barker et al.,
*Plant Mo. Biol.* (1983) 2:335-350) having deleted the AccI-sPhI fragment (bp 13800-13990).

pCGN451 pCGN451 contains an ocs5'-ocs3' cassette, including the T-DNA right border, cloned into a derivative of pUC8 (Vieira and Messing, supra). The modified vector is derived by digesting pUC8 with HincII and ligating in the presence of synthetic linker DNA, creating pCGN416, and then deleting the EcoRI site of pCGN416 by EcoRI digestion followed by treatment with Klenow enzyme and self-ligation to create pCGN426.

The ocs5'-ocs3' cassette is created by a series of steps from DNA derived from the octopine Ti-plasmid pTiA6 (Currier and Nester, supra). To generate the 5'end, which includes the T-DNA right border, an EcoRI fragment of pTiA6 (bp 13362-16202 (the numbering is by Barker, et al., (*Plant Mol. Bio* (1983) 2:335-350) for the closely related Ti plasmid pTil5955)) is removed from pVK232 (Knauf and Nester, *Plasmid* (1982) 8:45) by EcoRI digestion and cloned into EcoRI digested pACYC184 (Chang and Cohen, supra) to generate pCGN15.

The 2.4 kb BamHI-EcoRI fragment (bp 13774-16202) of pCGN15 is cloned into EcoRI-BamHI digested pBR322 (Bolivar, et al., supra) to yield pCGN429. The 412 bp EcoRI-BamHI fragment (bp 13362-13772) of pCGN15 is cloned into EcoRI-BamHI digested PBR322 to yield pCGN407. The cut-down promoter fragment is obtained by digesting pCGN407 with XmnI (bp 13512), followed by resection with Bal31 exonuclease, ligation of synthetic EcoRI linkers, and digestion with BamHI. Resulting fragments of approximately 130 bp are gel purified and cloned into M13mp9 (Vieira and Messing, supra) and sequenced. A clone, I-4, in which the EcoRI linker has been inserted at bp 1362 between the transcription initiation point and the translation initiation codon is identified by comparison with the sequence of de Greve, et al., (*J. Mol. Appl. Genet.* (1982) 1:499-512). The EcoRI cleavage site is at position 13639, downstream from the mRNA start site. The 141 bp EcoRI-BamHI fragment of I-4, containing the cut-down promoter, is cloned into EcoRI-BamHI digested pBR322 to create pCGN428. The 141 bp EcoRI-BamHI promoter piece from pCGN428, and the 2.5 kb EcoRI-BamHI ocs5' piece from pCGN429 are cloned together into EcoRI digested pUC19 (Vieira and Messing, supra) to generate pCGN442, reconstructing the ocs upstream region with a cut-down promoter section.

To generate the ocs3' end, the HindIII fragment of pLB41 (D. Figurski, UC San Diego) containing the gentamycin resistance gene is cloned into HindIII digested pACYC184 (Chang and Cohen, supra) to create pCGN413b. The 4.7 kb BamHI fragment of pTiA6 (supra), containing the ocs3' region, is cloned into BamHI digested pBR325 (F. Bolivar, *Gene* (1978) 4:121-136) to create 33c-19. The SmaI site at position 11207 (Barker, supra) of 33c-19 is converted to an XhoI site using a synthetic XhoI linker, generating pCCG401.2. The 3.8 kb BamHI-EcoRI fragment of pCGN401.2 is cloned into BamHI-EcoRI digested PCGN413b to create PCGN419.

Figure 7:
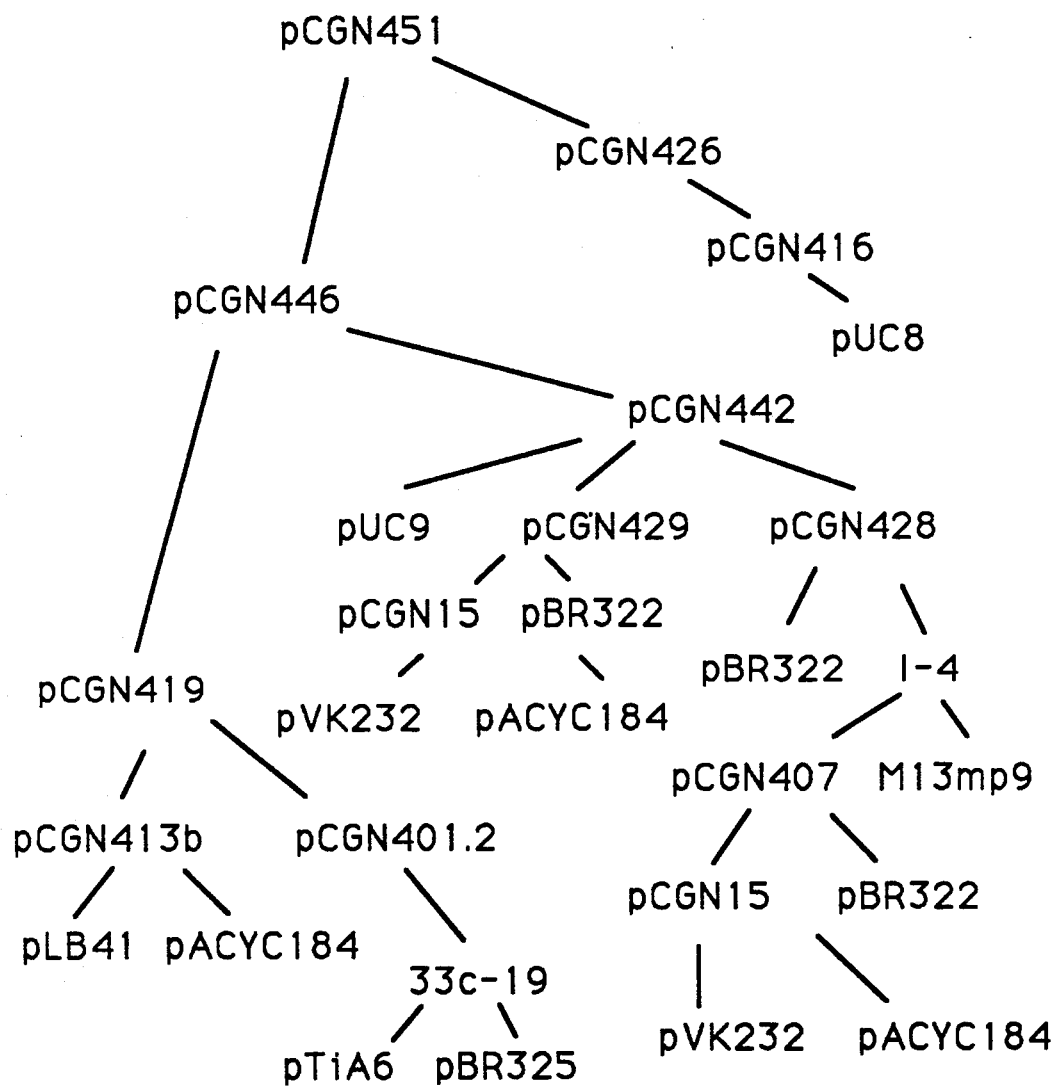
FIG. 7 is a schematic representation of the steps used to create pCGN451.

The ocs5'-ocs3' cassette is generated by cloning the 2.64 kb EcoRI fragment of pCGN442, containing the 5' region, into EcoRI digested pCGN419 to create pCNG446. The 3.1 kb XhoI fragment of pCNG446, having the ocs5' region (bp 13639-15208) and ocs3' region (bp 11207-12823), is cloned into the XhoI site of pCGN426 to create pCGN451 (FIG. 7).

D. pCGN65 construction.

pCGN501 is constructed by cloning a 1.85 kb EcoRI-XhoI fragment of pTiA6 (Currier and Nester, *J. Bact.* (1976) 126:157–165) containing bases 13362-15208 (Barker et al., *Plant Mo. Biol.* (1983) 2:335–350) of the T-DNA (right border), into EcoRI-SalI digested M13mp9 (Vieira and Messing, *Gene* (1982) 19:259–268). pCGN502 is constructed by cloning a 1.6 kb HindIII-SmaI fragment of pTiA6, containing bases 602-2212 of the T-DNA (left border), into HindIII-SmaI digested M13mp9. pCGN50I and pCGN502 are both digested with EcoRI and HindIII and both T-DNA-containing fragments cloned together into HindIII digested pUC9 (Vieira and Messing, *Gene* (1982) 19:259–268) to yield pCGN503, containing both T-DNA border fragments. pCGN503 is digested with HindIII and EcoRI and the two resulting HindIII-EcoRI fragments (containing the T-DNA borders) are cloned into EcoRI digested pHC79 (Hohn and Collins, *Gene* (1980) 11:291–298) to generate pCGN518 The 1.6kb KpnI-EcoRI fragment from pCGN518, containing the left T-DNA border, is cloned into KpnI-EcoRI digested pCGN565 to generate pCGN580. The BamHII-BglII fragment of pCGN580 is cloned into the BamHI site of pACYC184 (Chang and Cohen, *J. Bacteriol.* (1978) 134:1141–1156) to create pCGN51. The 1.4 kb BamHI-SphhI fragment of pCGN60 containing the T-DNA right border fragment, is cloned into BamHI-SphhI digested pCGN51 to create pCGN65, which contains the right and left T-DNA borders.

E. pCGN1537 construction.

pCGN65 is digested with KpnI and XbaI, treated with Klenow enzyme to create blunt ends, and ligated in the presence of synthetic BglII linker DNA to create pCGN65ΔKX. pCGN65ΔKX is digested with SalI, treated with Klenow enzyme to create blunt ends, and ligated in the presence of synthetic XhoI linker DNA to create pCGN65ΔKX-S+X. The 728 bp BglII-XhoI fragment of pCGN565RBa2X, containing the T-DNA right border piece and the lacZ' gene, is cloned into BglII-XhoI digested pCGN65ΔKX-S+X, replacing the right border fragment of pCGN65ΔKX-S+K. The resulting plasmid, pCGN65a2X, contains both T-DNA borders and the lacZ gene. The ClaI fragment pCGN65a2X is deleted and replaced with an XhoI linker by digesting with ClaI, treating with Klenow enzyme to create blunt ends, and ligating the presence of synthetic XhoI linker DNA to create pCGN65a2XX.

pCGN65a2XX is digested with BglII and fused with BglII digested pCGN549 (the gentamycin resistance gene is isolated from a 3.1 kb EcoRI-PstI fragment of PPHIJI, Hirsch et al., *Plasmid* (1984) 12:139–141 and cloned into pUC9, Vieira et al., *Gene* (1982) 19:259–268, yielding pCGN549) to create pCGN1530 which contains both plasmid backbones. pCGN1530 is digested with XhoI and religated, then a gentamycin-resistant chloramphenicol-sensitive clone is chosen from the pACYC184-derived backbone has been deleted, creating pCGN1530A. The 2.43 kb XhoI fragment of pCGN1536, containing the mas5'-kan-mas3' cassette, is cloned into XhoI digested pCGN1530A to create pCGN1537.

F. Final assembly of pCGN1540.

The BglII fragment of pCGN1537, containing the plant selectable marker gene and the lacZ' screenable marker gene (with multiple cloning site), all between the T-DNA borders, is cloned into BamHI digested pCGN1532. A clone of the orientation bearing the T-DNA right border adjacent to the Ri plasmid origin of replication is designated pCGN1540. This binary vector has several advantageous features, including a minimal amount of DNA between the T-DNA borders, high stability in Agrobacterium hosts, high copy number in *E. coli* hosts, and a blue/white screen with multiple restriction enzyme sites for ease of cloning target DNA.

The plasmid pCGN1540 has been deposited with ATCC (Rockville, Md.), accession number 40586, dated Mar. 21, 1989.

2. Double UAR CaMV 35S/Mas Promoter pCGN2113 (see below) is digested with HindIII and SalI. The cohesive ends are blunted by mung bean nuclease, and XhoI linkers 5' CCTCGAGG 3' are inserted into the blunt ends to create an XhoI site The resulting construct, pCGN7300, is digested and religated with PstI after removal of a EcoRV restriction site situated between flanking PstI sites creating pCGN7300ΔEcoRV.

pCGN7000, described above, is digested with EspI and PstI to provide a fragment containing a trucated mas region (300 bp with TATA box), a gene encoding β-glucuronidase (GUS) and a termination region (mas 3'). PCGN7300ΔEcoRV is digested with EcoRV and PstI to provide a fragment containing approximately 800-850 bp of the upstream region with the double enhancer of CaMV 35S promoter and approximately 150 bp of the tml' region. The EspI-PstI fragment of pCGN7000 and the EcoRV-Pst fragment of pCGN7300ΔEcoRV are ligated to create p004B-1 having approximately 300 bp of the mas transcript/translation regulatory region and an upstream region having a double enhancer region from 35 CaMV (the "Double Mac").

p004B-1 is digested with xHOI and ligated to XhoI site of pCGN7329, described above, to create pCGN7336. After digestion with PstI, the fragment having the Double MAC-gus-mas3' sequences is inserted into the PstI site of the binary vector pCGN1540, described above.

Construction of pCGN2113 pCGN2113 contains a double-35S promoter and the tml-3' region with multiple cloning sites between them, contained in a pUC-derived plasmid backbone bearing a ampicillin resistance gene; the promoter/a tml cassette is bordered by multiple restriction sites for easy removal. pCGN2113 is derived from pCGN986, pCGN164, and pCGN638.

1. Construction of pCGN986. pCGN986 contains a cauliflower mosaic virus 35S (CaMV35) promoter and a T-DNA tml 3'-region with multiple restriction sites between them. pCGN986 is derived from another cassette, pCGN206, containing a CaMV35S promoter and a different 3' region, the CaMV region VI 3'-end. The CaMV 35S promoter is cloned as an AluI fragment (bp 7114–7734) (Gardner et. al., *Nucl. Acids Res.* (1981) 9:2871–2888) into the HincII site of M13mp7 (Messing et. al., *Nucl. Acids Res.* (1981) 9:309–321) to create C614. An EcoRI digest of C614 produces the EcoRI fragment from C614 containing the 35S promoter which is cloned into the EcoRI site of pUC8 (Viera and Messing, *Gene* (1982) 19:259) to produce pCGN147.

pCGN148a containing a promoter region, selectable marker (KAN with 2 ATG's) and 3' region, is prepared by digesting pCGN528 with BglII and inserting the BamHI-BglII promoter fragment from pCGN147. This fragment is cloned into the BglII site of pCGN528 so that the BglII site is proximal to the kanamycin gene of pCGN528.

The shuttle vector used for this construct, pCGN528, is made as follows: pCGN525 is made by digesting a plasmid containing Tn5, which harbors a kanamycin gene (Jorgenson et. al., *Mol. Gen. Genet.* (1979) 177:65), with HindIII-BamHI and inserting the HindIII-BamHI fragment containing the kanamycin gene into the HindIII-BamHI sites in the tetracycline gene of pACYC184 (Chang and Cohen, *J. Bacteriol.* (1978) 134:1141–1156). pCGN526 is made by inserting the BamHI fragment 19 of pTiA6 (Thomashow et. al., Cell (1980) 19:729–739), modified with XhoI linkers inserted into the SmaI site, into the BamHI site of pCGN525. pCGN528 is obtained by deleting the small XhoI fragment from pCGN526 by digesting with XhoI and religating.

pCGN149a is made by cloning the BamHI-kanamycin gene fragment from pMB9KanXXI into the BamHI site of pCGN148a. pMBG9KanXXI is a PUC4K variant (Vieira and Messing, *Gene* (1982) 19:259–268) which has the XhoI site missing, but contains a functional kanamycin gene from Tn903 to allow for efficient selection in Agrobacterium.

pCGN149a is digested with HindIII and BamHI and ligated to pUC8 digested with HindIII and BamHI to produce pCGN169. This removes the Tn903 kanamycin marker. pCGN565 (see above) and pCGN169 are both digested with HindIII and PstI and ligated to form pCGN203, a plasmid containing the CaMV 35S promoter and part of the 5'-end of the Tn5 kanamycin gene (up to the PstI site, Jorgenson et. al., (1979), supra). A 3'-regulatory region is added to pCGN203 from pCGN204 (an EcoRI fragment of CaMV (bp 408–6105) containing the region VI 3' cloned into pUC18 (Gardner et. al., (1981) supra) by digestion with HindIII and PstI and ligation. The resulting cassette, pCGN206, is the basis for the construction of pCGN986.

The pTiA6 T-DNA tml 3'-sequences are subcloned from the Bam19 T-DNA fragment (Thomashow et al., (1980), supra) as a BamHI-EcoRI fragment (nucleotides 9062 to 12,823, numbering as in Barker et. al., *Plant Mol. Biol.* (1983) 2:335–350) and combined with the pACYC184 (Chang and Cohen (1978), supra) origin of replication as an EcoRI-HindIII fragment and a gentamycin resistance maker (from plasmid pLB41, obtained from D. Figurski) as a BamHI-HindIII fragment to produce pCGN417.

The unique SmaI site of pCGN417 (nucleotide 11,207 of the Bam19 fragment) is changed to a SacI site using linkers and the BamHI-SacI fragment is subcloned into pCGN565 to give PCGN971. The BamHI site of pCGN971 is changed to an EcoRI site using linkers and created pCGN971E. The resulting EcoRI-SacI fragment containing the tml 3' regulatory sequences is joined to pCGN206 by digestion with EcoRI and SacI to give pCGN975. The small part of the Tn5 kanamycin resistance gene is deleted from the 3'-end of the CaMV 35S promoter by digestion with SalI and BglII, blunting the ends and ligation with SalI linkers. The final expression cassette, pCGN986, contains the CaMV 35S promoter followed by two SalI sites, and XbaI site, BamHI, SmaI, KpnI and the tml 3' region (nucleotides 11207-9023 of the T-DNA).

2. Construction of pCGN164. The AluI fragment of CaMV (bp 7144–7735) (Gardner et. al., *Nucl. Acids Res.* (1981) 9:2871–2888) is obtained by digestion with AluI and cloned in to the HincII site of M13mp7 (Vieira et al., *Gene* (1982) 19:259) to create C614. An EcoRI digest of C614 produced the EcoRI fragment from C614 containing the 35S promoter which is cloned into the EcoRI site of pUC8 (Vieira et al., (1982) ibid) to produce pCGN146. To trim the promoter region, the BglII site (bp7670) is treated with BglII and Bal31 and subsequently a BglII linker was attached to the Bal31 treated DNA to produce pCGN147. pCGN147 is digested with EcoRI and HphI and the resultant EcoRI-HphI fragment containing the 35S promoter is ligated into EcoRI-SmaI digested M13mp8 to create pCGN164.

3. Construction of pCGN638. Digestion of CaMv10 (Gardner et al., (1981) supra) with BglII produces a BglII fragment containing a 35S promoter region (bp 6493-7670) which is ligated into the BamHI site of pUC19 (Norrander et al., *Gene* (1983) 26:101–106) to create pCGN638.

4. Construction of pCGN2113. pCGN164 is digested with EcoRV and BamHI to release a EcoRV-BamHI fragment which contains a portion of the 35S promoter (bp 7340-7433); pCGN638 is digested with HindIII and EcoRV to release a HindIII-EcoRV fragment containing a different portion of the 35S promoter (bp 6493-7340). These two fragments are ligated into pCGN986 which has been digested with HindIII and BamHI to remove the HindIII-BamHI fragment containing the 35S-promoter; this ligation produced pCGN639, which contains the backbone and tml-3' region from pCGN986 and the two 35S promoter fragments from pCGN164 and pCGN638. pCGN638 is digested with EcoRV and DdeI to release a fragment of the 35S promoter (bp 7070-7340); the fragment is treated with the Klenow fragment of DNA polymerase I to create blunt ends, and is ligated into the EcoRV site of pCGN639 to produce pCGN2113 having the fragment in the proper orientation.

The plasmid pCGN2113 has been deposited with the ATCC (Rockville, Md.) accession number 40587, dated Mar. 2, 1989.

3. UAR CaMV 35S/Long Mas Promoter pCGN1154A (described above) is digested with EcoRV and XbaI, deleting the TATA-box-containing region of the 35S promoter. In its place, a fragment containing the TATA box and about 685 pairs of the 5' upstream region of the mas transcription/translation regulatory region (specifically, bp 20128-20807 according to numbering of Barker et al. (supra) (fragment is generated by digesting pCGN40 (described above) with NaeI and XbaI) is inserted. The resulting plasmid, pCGN1160, contains the hybrid UAR of CaMV35S/-long mas promoter.

Construction of the Binary Vector pCGN7390

Figure 5:
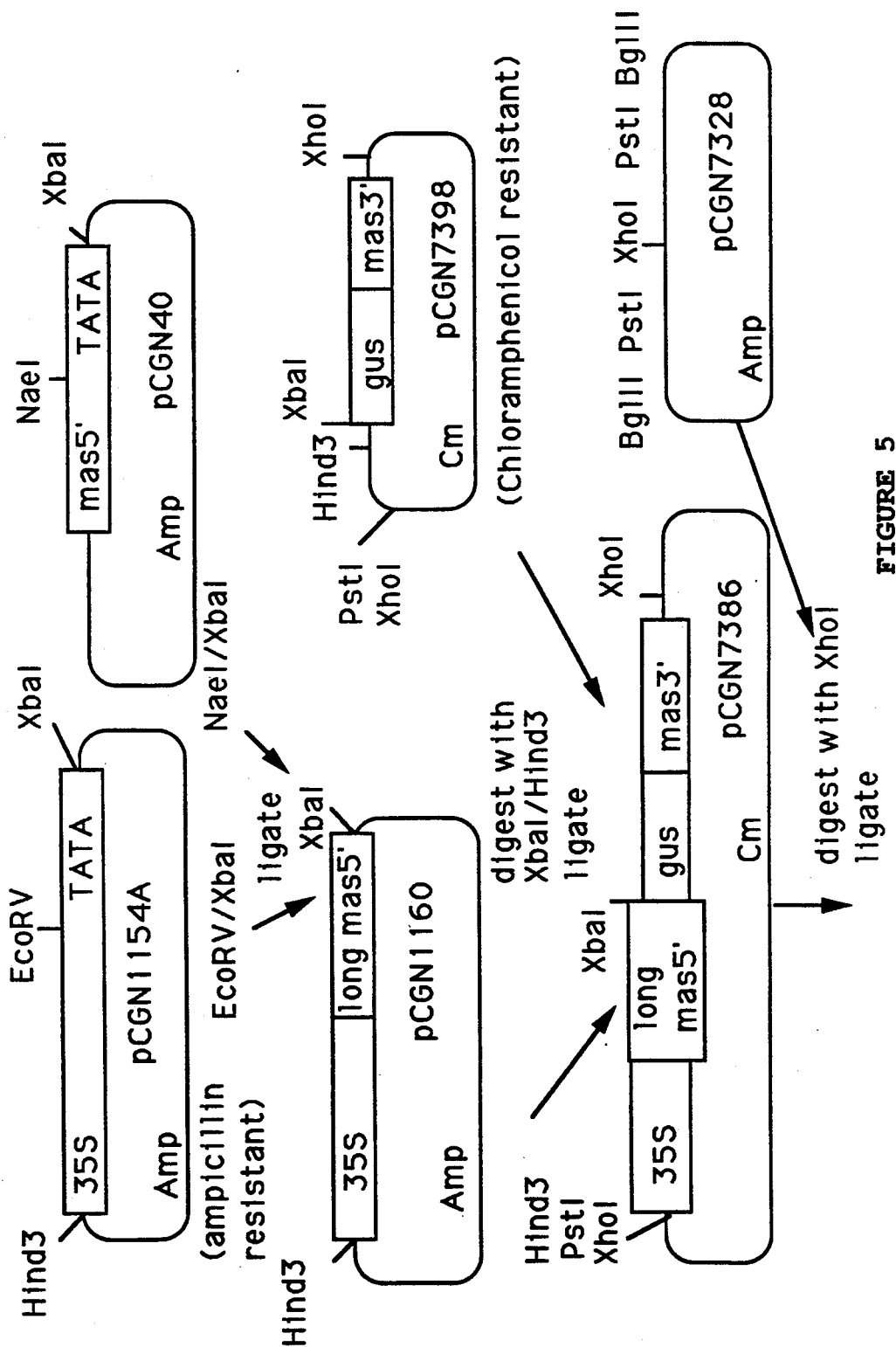
FIG. 5 is a schematic representation of the final construction steps of pCGN7390.
Figure 5:
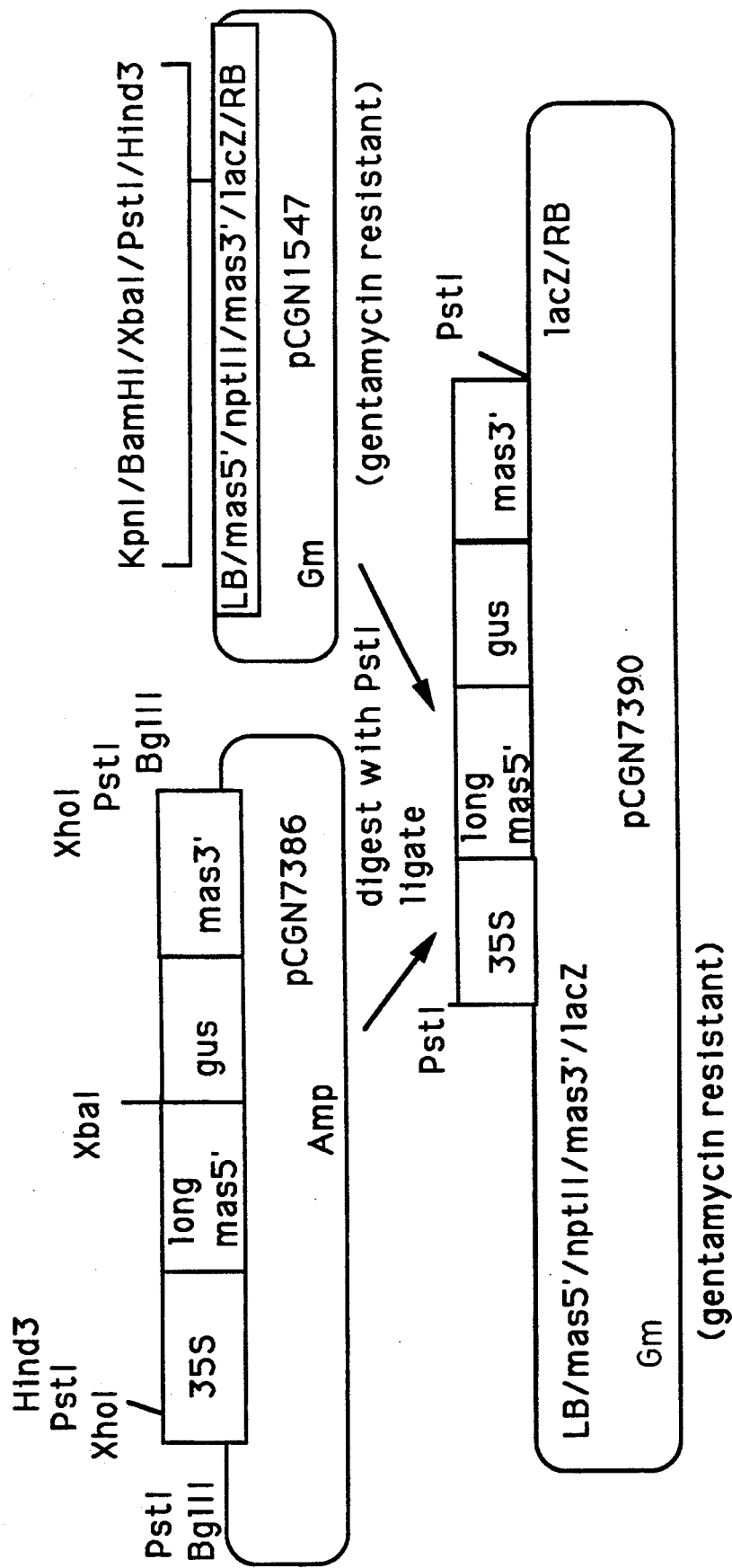

The 1.5 kb 35S/long-mas-containing fragment of pCGN1160 (see above) is removed by digestion with XbaI and HindIII and ligated with XbaI/HindIII-digested pCGN7398 (see below). The resulting plasmid, pCGN7386, contains CaMV 35S/long mas5'-gus-mas 3'. pCGN7386 is digested with XhoI and the fragment containing the CaMV 35S/long mas5'-gus-mas3'is cloned into the XhoI site of converter plasmid pCGN7328 (see below), resulting in pCGN7388, which is resistant to ampicillin. The 35S/long mas 5'-gus-mas3' is removed from pCGN7388 as a PstI fragment and cloned into the PstI site of pCGN1547 (see below), resulting in the binary vector pCGN7390 (FIG. 5).

Construction of pCGN7398 pCGN7000 (described above) is digested with BamHI and PstI. The 2.7 kb fragment carrying the gus gene and the mas3' region is cloned into the BamHI/PstI sites of pCGN7300 (described above), resulting in plasmid "5-90-12". "5-90-12" is digested with XhoI and the 3.9 kb fragment carrying the double 35S-gus-mas3' region is ligated with XhoI-digested pCGN1003 (described above), resulting in pCGN7304. pCGN7304 is digested with XhoI and BamHI to delete the 1.2 kb double 35S region. This region is replaced with a single 35S region, carried on an XbaI/BamHI fragment obtained from pCGN639 (described above). The resulting plasmid, carrying the single 35S-gus-mas3' region, is called "8-46A-1". The SmaI site of "8-46A-1" is replaced with an XbaI site by ligating SmaI digested "8-46A-1" with XbaI linker DNA, resulting in the plasmid "9-47-19". The 35S region is deleted from "9-47-19" as an XbaI fragment, and is replaced with a polylinker containing unique restriction sites for PstI, SphI, NotI, KpnI, BglII, HindIII, SmaI, SalI and XbaI, resulting in PCGN7398. pCGN7398 contains gus-mas3', with multiple cloning sites in front of gus.

Construction of pCGN7328 pCGN7328 is generated by digesting pUC19 with HindIII and EcoRI and ligating in a polylinker containing HindIII/BglII/PstI/XhoI/PstI/BglII/EcoRI.

Construction of pCGN1547

PCGN1547 (parts of which are described in co-pending U.S. patent application Ser. No. 07/364,362) is a binary plant transformation vector containing the left and right T-DNA borders of *Agrobacterium tumefaciens* octopine Ti-plasmid pTiA6 (Currier and Nester, supra), the gentamycin resistance gene of pPh1JI (Hirsch and Beringer, supra), an *Agrobacterium rhizogenes* Ri plasmid origin of replication from pLJbB11 (Jouanin et al., supra), the mas promoter region and mas 3' region of pTiA6 with the kanamycin resistance gene of Tn5 (Jorgensen et al., supra), a ColE1 origin of replication from pBR322 (Bolivar et al., supra), and a lacZ' screenable marker gene from pUC18 (Yannisch-Perron et al.,supra).

There are three major intermediate constructs used to generate pCGN1547:

pCGN1532 (See PCGN1540 description) is made up of the pCGN1547 backbone, the pRi plasmid origin of replication, and the ColE1 origin of replication.

pCGN1536 (See pCGN1540 description) contains the mas5'-kan-mas3' plant selectable marker region.

pCGN1541b contains the right and left T-DNA borders of the *A.tumefaciens* octopine Ti-plasmid, and the lacZ' region, with multiple cloning sites (to use as a screenable marker in bacteria), from pUC19. The construction of this plasmid is described below.

Figure 6:
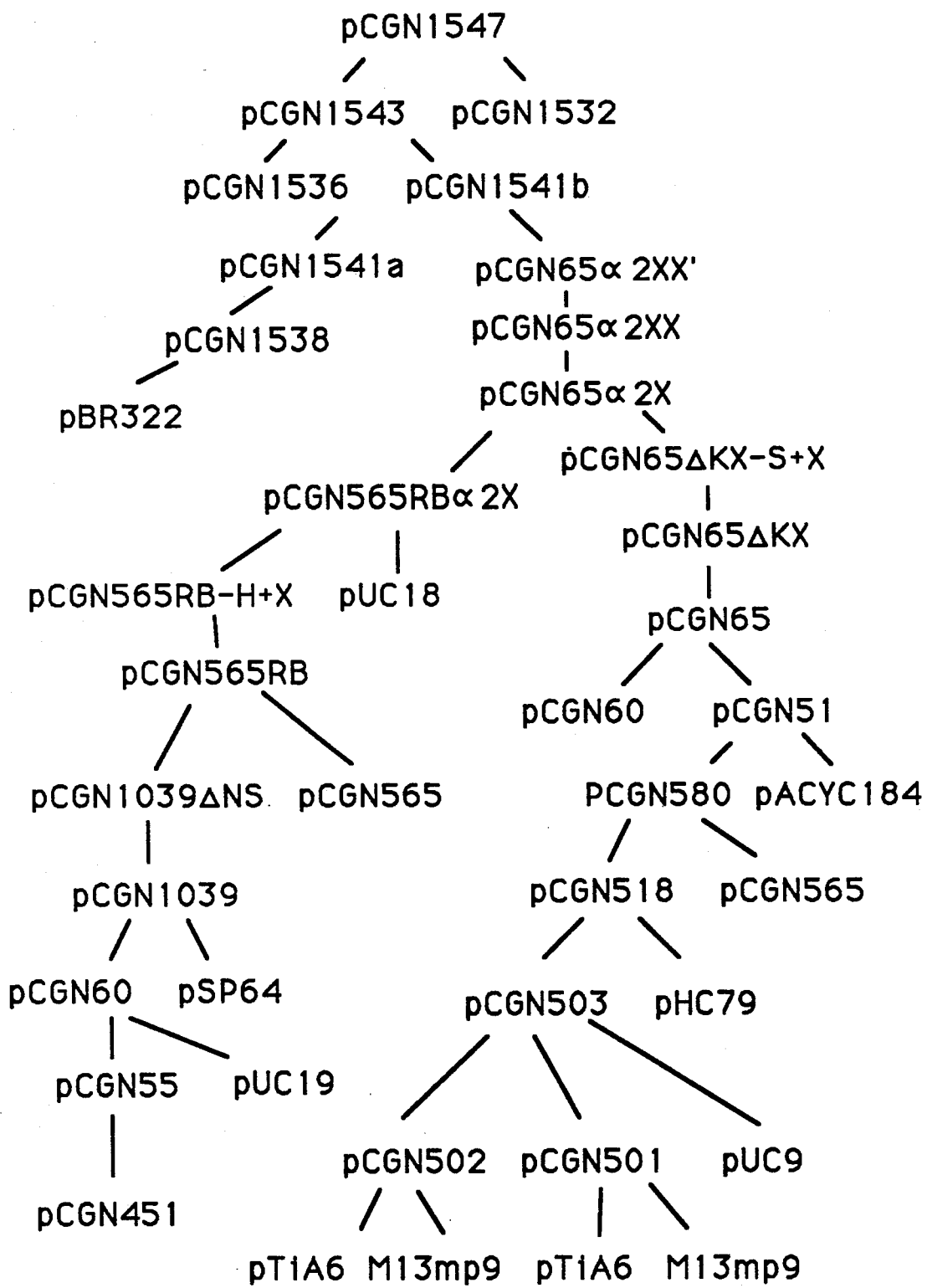
FIG. 6 is a schematic representation of the steps used to create pCGN1547.

To construct pCGN1547 from the above plasmids, pCGN1536 is digested with XhoI, and the fragment containing the mas5'-kan-mas3' region is cloned into the XhoI site of pCGN1541b to give the plasmid pCGN1543, which contains T-DNA left border-mas5'-kan-mas3'-lacZ'-T-DNA right border. pCGN1543 is digested with BglII, and the fragment containing the T-DNA left border-mas5'-kan-mas3'865-lacZ'-right border region is ligated into BamHI-digested pCGN1532 to give the complete binary vector, pCGN1547 (FIG. 6).

Construction of pCGN1541b pCGN565RBα2X (see pCGN1536 construction) is digested with BglII and XhoI, and the 728bp fragment containing the T-DNA right border piece and the lacZ' gene is ligated with BglII-XhoI digested pCGN65ΔKX-S+K (see pCGN1537 construction), replacing the BglII-XhoI right border fragment of pCGN65ΔKX-S+K. The resulting plasmid, pCGN65α2X contains both T-DNA borders and the lacZ' gene. The ClaI fragment of pCGN65α2X is replaced with an XhoI site by digesting with ClaI blunting the ends using the Klenow fragment, and ligating with XhoI linker DNA, resulting in plasmid PCGN65α2XX. pCGN65α2XX is digested with BglII and EcoRV, treated with the Klenow fragment of DNA polymerase I to create blunt ends, and ligated in the presence of BglII linker DNA, resulting in pCGN65α2XX'. PCGN65α2XX' is digested with BglII and ligated with BglII digested pCGN1538 (see below), resulting in pCGN1541a, which contains both plasmid backbones. pCGN1541a is digested with XhoI and religated. Ampicillin resistant, chlormaphenicol sensitive clones are chosen, which lack the pACYC184-derived backbone, creating pCGN1541b.

pCGN1538 is generated by digesting pBR322 with EcoRI and PvuII, treating with Klenow to generate blunt ends, and ligating with BglII linkers. pCGN1538 is ampicillin resistant, tetracycline sensitive.

4. Comparative Study/Double 35S CaMV

For comparison, a double CaMV 35S promoter is prepared having the gus reporter gene with the mas 3' end which is spliced into the binary vector pCGN1540. The double 35S promoter is a 1.2 kb fragment obtained from pCGN2113 having nucleotide sequences −941 to −90, joined to a sequences −363 to −90 and −90 to −2 of the CaMV 35S promoter region.

Generation of Transgenic Plants

1. Tomato

Sterile tomato cotyledon tissue is obtained from 7-8 day old seedlings which are grown at 24° C., with a 16 hr/8 hr day/night cycle, or alternatively, or 12 hr./12 hr. day/night cycle, in 100×25 mm petri dishes containing MSSV medium: Murashige-Skoog(MS) salts (#1117 Gibco Laboratories, New York), sucrose 30 g/l, Nitsch vitamins (Thomas, B. R., and Pratt, D. *Appl. Genet.* (1981) 59:215-219), 0.8% agar (pH 6.0). Any tomato species may be used. However, the inbred breeding line UC82B (Department of Vegetable Crops, University of California, Davis) is preferred. The tips and bases of the cotelydons are removed and the center section placed onto a feeder plate for a 24-hour preincubation period in low light (30–40 $\mu Em^{-2}S-1$) at 24° C.

The feeder plates are prepared by pipetting 0.5 ml of an eight day old suspension of *Nicotiana tabacum* cv *xanthi-nc* cell suspension culture (~$10^6$ cells/ml) onto 0.8% agar medium, containing MS salts, myo-inositol (100 mg/l), thiamine-HCL (1.3 mg/l), sucrose (30 g/l), potassium acid phosphate (200 mg/l) 2,4-D (0.2 mg/l), and kinetin (0.1 mg/l) (pH 5.5). The feeder plates are prepared one day prior to use. A #1 Whatman sterile filter paper(Whatman Ltd Maidstone, England) is placed on top of the tobacco cells after the suspension cells have grown for at least one day.

The Agrobacterium containing the binary construct are grown on AB medium (AB salts K₂HPO₄ 3 gm/l, NaH₂PO₄.H₂O 1.15 g/l, NH₄CL 1 g/l, glucose 5 g/l, FeSO₄ 0.25 mg/l, MgSO₄ 0.246 mg/l, 0.14 mg/l, 15 g/l agar 100 μg/l gentamycin sulfate and 100 μg/l streptomycin sulfate) for 4-5 days. Single colonies are then inoculated into 5 mls of MG/L broth and are incubated overnight in a shaker at 30° C. and 180 R.P.M. Following the preincubation period, the cotyledon explants are dipped into the bacterial suspension of $5 \times 10^8$ bacteria/ml for approximately 5 minutes, blotted on sterile paper towels and returned to the original tobacco feeder plates. The explants are then cocultivated with the bacteria for 48 hours on the tobacco feeders plates in low light (30-40 $\mu Em^{-2}S-1$) at 24° C. The explants are then transferred to regeneration medium containing 500 mg/l of carbenicillin disodium salts and at least 100 mg/l of kanamycin sulfate. The regeneration medium is MS salts medium with zeatin (2 mg/l), myo-inositol (100 mg/l), sucrose (20 g/l), Nitsch vitamins and 0.8% agar (pH 6.0). The explants are then transferred to fresh regeneration medium containing 500 mg/l of carbenicillin disodium salts and at least 100 mg/l of kanamycin sulfate at 10 days and subsequently every three weeks. Shoots are harvested from 8 weeks onwards and placed on MSSV medium containing carbenicillin (50 mg/l), kanamycin (50 mg/l) and indole-3-butyric acid (1 mg/l). Roots develop in 7-14 days. Plants are then transplanted into soil.

2. Tobacco

Tobacco leaf explants, roughly 5-10 mm by 5-10 mm, are cut from young leaves, approximately 3-5 cm long and third to sixth from the apex of *Nicotiana tabacum cv xanthi-nc* which have been grown under axenic conditions in solid medium: Murashige Minimal Organics (#1118 Gibco Laboratories, New York), 7% phytagar, 1 mg/l indole-3-acetic acid, 0.15 mg/l kinetin. The explants are plated on solid medium containing Murashige Minimal Organics, 6% phytagar, 40 mg/l adenine sulfate, 2 mg/l indoe-3-acetic acid, 2 mg/l kinetin. A sterile #1 Whatman filter paper (Whatman Ltd., Maidstone, England) is placed on the top of the plate medium and they are incubated for 24 hours in the dark at 24° C.

The Agrobacterium containing the binary construct are grown on AB medium (AB salts K₂HPO₄ 3 gm/l, NaH₂PO₄.H₂O 1.15 g/l, NH₄Cl 1 g/l, glucose 5 g/l, FeSO₄ 0.25 mg/l, MgSO₄ 0.246 mg/l, 0.14 mg/l, 15 g/l agar, 100 μg/l gentamycin sulfate and 100 μg/l streptomycin sulfate) for 4-5 days. Single colonies are inoculated into 5 mls of MG/L broth (50% Luria broth and 50% mannitol-glutamate salts medium (Garfinkel and Nester, *J.Bacteriol.* (1980)144:732-743)) and are incubated overnight in a shaker at 30° C. and 180 R.P.M. before co-cultivation.

Following the preincubation period, the explants are dipped into the bacterial suspension of $3.3 \times 10^8$ cells/ml for approximately 5 minutes, blotted on sterile paper towels and replated on the same plates. After 48 hours, the explants are placed on selection medium containing the same plate medium as above plus 350 mg/l cefotaxime and 100 mg/l kanamycin. The explants are transferred to fresh media every 2 weeks. At the 6 week transfer and thereafter, shoot and green callus are trimmed from explants and placed on solid media: Murashige Minimal Organics, 0.5 mg/l indole-3-acetic acid, 2 mg/l kinetin, 40 mg/l adenine sulfate, 350 mg/l cefotaxime, 100 mg/l kanamycin. Shoots may be harvested beginning about 4 weeks after co-cultivation and placed in 50 ml culture tubes with 25 ml of solid medium (7% bactagar 1 mg/l indole-3-butyric acid, 350 mg/l cefotaxime, 100 mg/l kanamycin) and grown at 24°-28° C., 12 hours light, 12 hours dark, light intensity 80-100uEm$^{-b2}$s$^{-1}$. Shoots root in 1-2 weeks and are then transplanted into soil and placed in growth chambers.

3. Results

Figure 4A:
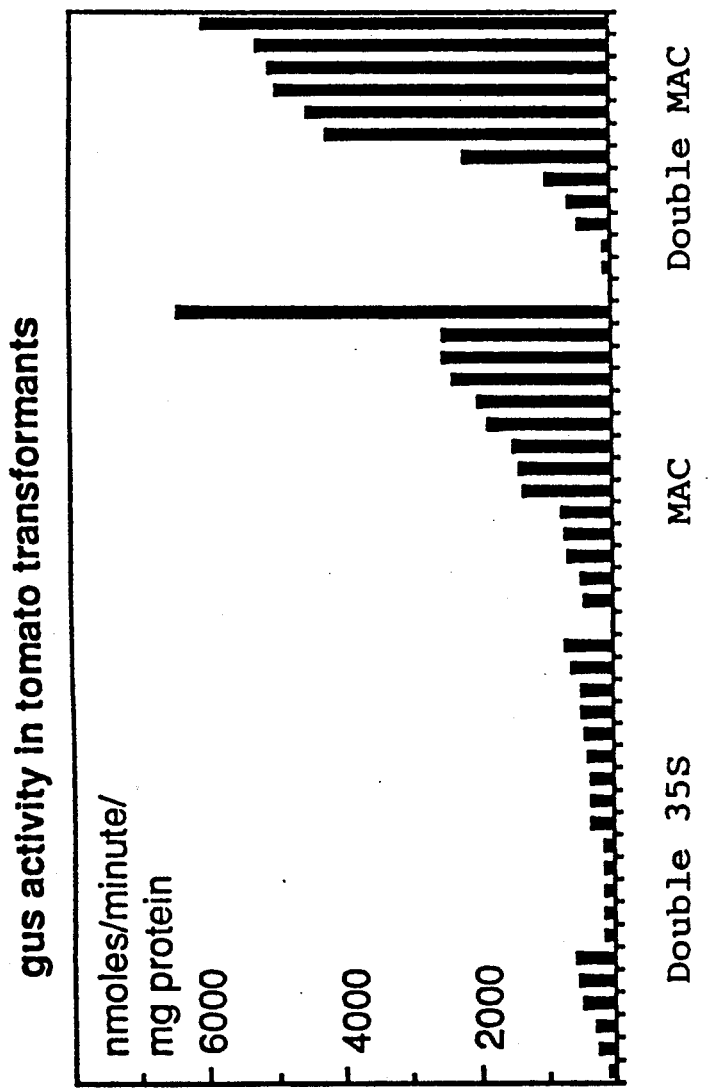
FIG. 4 is a graph showing a comparison of gus activity of several transformants under the control of transcription/translation initiation region having a double CaMV 35S promoter, a CaMV 35S enhanced mas promoter ("MAC"), or a double CaMV 35S enhanced mas promoter ("Double MAC").
Figure 4B:
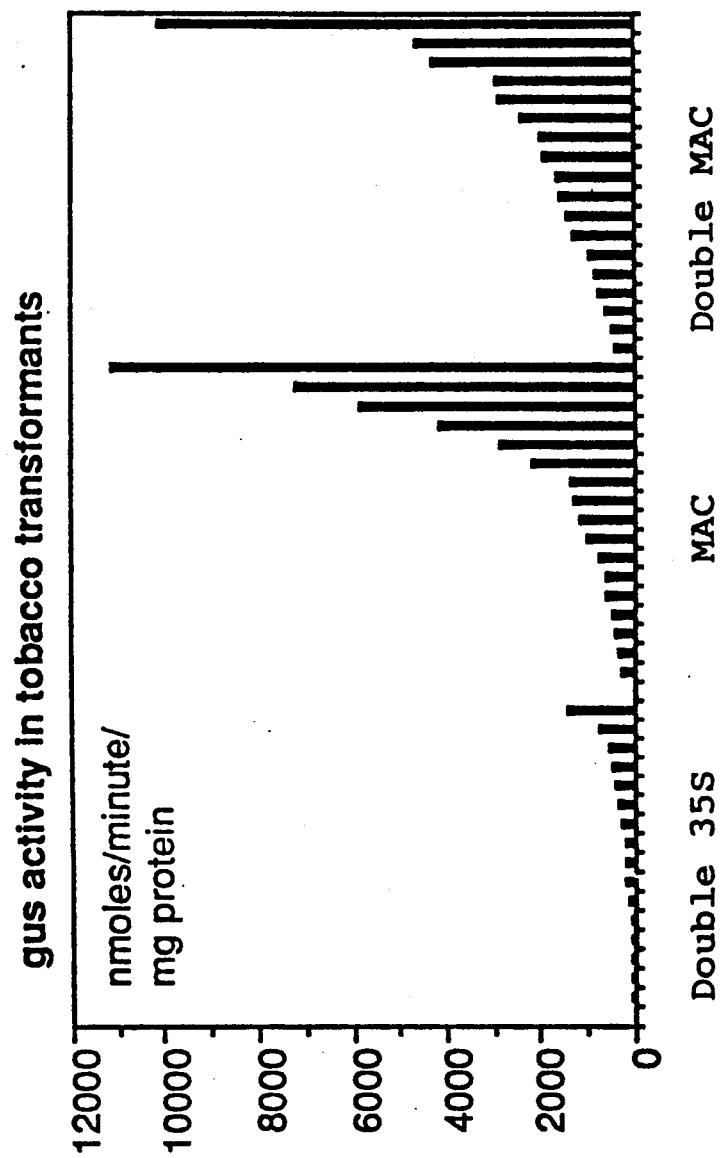

Plants are maintained in growth chambers and young leaves 2 to 3 cm in length are harvested from plants at the 6 to 10 leaf stage. Gus activity was measured in leaf extracts and expressed as units of activity for mg of protein according to the methods of Jefferson, R. A., *Plant Mol.Biol.Rep.* (1987)5:387-405. FIG. 4 shows a comparison of the activity of several tomato and tobacco transformants screened for gus activity. As expected the level of expression varies several folds. However, the average expression level is 5 to 10 fold higher in plants transformed with the marker under the regulatory control of the MAC promoter or the Double MAC promoter than with the double CaMV 35s promoter.

The above results demonstrate that the MAC, and the Double MAC, promoters are expressed at higher levels in plants than the same construct under the control of the Double 35S CaMV promoter. The results show significant and synergistic improvements to the mas promoter when enhanced by the upstream activating region of the CaMV 35S gene.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teachings of this invention that certain changes and modifications may be made thereto without departing from the spirit or scope of the appended claims.

What is claimed is:

1. A DNA sequence comprising, in the 5' to 3' direction, a first element linked to a second element, said first element comprising an upstream activating region of CaMV 35S and said second element comprising a mannopine synthase transcription initiation region.

2. A DNA sequence of claim 1 wherein said second element comprises a transcription/translation initiation region of mannopine synthase.

3. The DNA sequence of claim 1 wherein said first element comprises two upstream activating regions of CaMV 35S.

4. The DNA sequence of claim 1 wherein said first element comprises approximately from at least about −360 to about −25 of the CaMV 35S gene.

5. The DNA sequence of claim 1 wherein said second element comprises approximately from at least about −300 to about +60 of the mannopine synthase gene.

6. The DNA sequence of claim 1 wherein said second element comprises approximately from at least about −625 to about +60 of the mannopine synthase gene.

7. The DNA sequence of claim 1 wherein said upstream activating element comprises approximately from about −360 to −90 of the CaMV 35S gene.

8. The DNA sequence of claim 1 further comprising, in the 5' to 3' direction, said second element linked to a third element, wherein said third element comprises one or more nucleic acid sequences of interest.

9. A chimeric promoter comprising a CaMV 35S enhanced mannopine synthase promoter, wherein upon expression of a DNA sequence of interest in a plant cell under the regulatory control of said promoter, said DNA sequence of interest is expressible at a level of at least 5-fold higher than expression of said gene of interest in a plant cell under the regulatory control of a CaMV 35S enhanced CaMV 35S promoter.

10. The chimeric promoter of claim 9 wherein said mannopine synthase promoter is enhanced by a truncated CaMV 35S gene comprising an upstream activating region of a CaMV 35S promoter positioned 540 to said manopine synthase promoter.

11. The chimeric promoter of claim 9 comprising, in the 5' to 3' direction, a first element linked to a second element, said first element comprising a DNA sequence corresponding to approximately about a 200 bp to about 850 bp fragment of the upstream activating region of CaMV 35S and said second element comprising a DNA sequence corresponding to approximately about an 325 bp to about 875 bp fragment of the transcription/translation initiation region of the mannopine synthase gene.

12. The chimeric promoter of claim 9 wherein said first element is from about −360 to about −90 of the CaMV 35S gene and said second element is from about −300 to about +60 of the mannopine synthase gene.

13. The chimeric promoter of claim 9 wherein said first element is from about −360 to about −90 of the CaMV gene and said second element is from about −625 to +60 of the mannopine synthase gene.

14. The chimeric promoter of claim 9 wherein said said gene of interest is expressible at a level of at least 10-fold higher than expression of the gene of interest in a plant cell under the regulatory control of a CaMV 35S enhanced CaMV 35S promoter.

15. The chimeric promoter of claim 9 wherein said DNA sequence is expressed in an in vivo plant cell.

16. A method to increase the expression of an expressible gene of interest under the regulatory control of a mannopine synthase promoter comprising the steps of:
providing a CaMV 35S upstream activating region to the 5' end of a DNA sequence comprising the mannopine synthase promoter; and
allowing said gene to be expressed.

17. The method of claim 16 wherein said CaMV 35S upstream activating region comprises a DNA sequence corresponding to approximately about an 200 bp to about 850 bp fragment of the upstream activating region of CaMV 35S and said mannopine synthase promoter comprises a DNA sequence corresponding to approximately about an 325 bp to about 800 bp fragment from the transcript/translation initation region of the mannopine synthase gene.

18. The method of claim 17 wherein said CaMV 35S upstream activation region comprises from about −300 to about −90 of the CaMV gene and said mannopine synthase promoter comprises from about −300 to about +60 of the mannopine synthase gene.

19. The method of claim 17 wherein said CaMV 35S upstream activation region comprises from about −300 to about −90 of the CaMV gene and said mannopine synthase promoter comprises from about −625 to about +60 of the mannopine synthase gene.

20. The method of claim 16 wherein said gene of interest is expressed in a plant cell.

21. The method of claim 16 wherein said gene of interest is expressed in vivo.

* * * * *

UNITED STATES PATENT AND TRADEMARK OFFICE
CERTIFICATE OF CORRECTION

PATENT NO. : 5,106,739

DATED : April 21, 1992

INVENTOR(S) : Luca Comai, Paul M. Moran

It is certified that error appears in the above-identified patent and that said Letters Patent is hereby corrected as shown below:

The sheet of Drawing consisting of Fig.3, should be added a shown on the attached sheet.

Signed and Sealed this

Fourteenth Day of September, 1993

Attest:

BRUCE LEHMAN

Attesting Officer     Commissioner of Patents and Trademarks